(12) United States Patent
Mrozek et al.

(10) Patent No.: US 10,369,248 B2
(45) Date of Patent: Aug. 6, 2019

(54) POROUS POLYMER COMPOSITES

(71) Applicant: U.S. Army Research Laboratory ATTN: RDRL-LOC-I, Adelphi, MD (US)

(72) Inventors: Randy A. Mrozek, Baltimore, MD (US); Joseph L. Lenhart, Port Deposit, MD (US); Michael C. Berg, Baltimore, MD (US); Eric J. Robinette, Wilmington, DE (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 14/445,089

(22) Filed: Jul. 29, 2014

(65) Prior Publication Data

US 2016/0030625 A1   Feb. 4, 2016

(51) Int. Cl.
   *C08J 9/26* (2006.01)
   *C08J 9/28* (2006.01)
   *A61L 24/00* (2006.01)

(52) U.S. Cl.
   CPC ....... *A61L 24/0036* (2013.01); *A61L 24/0015* (2013.01); *C08J 9/26* (2013.01); *C08J 9/28* (2013.01); *A61L 2300/418* (2013.01); *A61L 2400/04* (2013.01); *A61L 2400/08* (2013.01); *C08J 2201/0543* (2013.01); *C08J 2207/10* (2013.01); *C08J 2207/12* (2013.01); *C08J 2353/02* (2013.01)

(58) Field of Classification Search
   None
   See application file for complete search history.

(56) References Cited

U.S. PATENT DOCUMENTS

| | | | |
|---|---|---|---|
| 7,109,249 B2 | 9/2006 | Bruza et al. | |
| 2005/0077221 A1* | 4/2005 | Berg | B01J 20/26 210/198.2 |
| 2006/0233887 A1* | 10/2006 | Day | 424/602 |
| 2006/0263335 A1* | 11/2006 | France | A61L 27/54 424/93.7 |

FOREIGN PATENT DOCUMENTS

WO   WO 07126411   * 11/2007

OTHER PUBLICATIONS

Mikos et al. Preparation and Characterization of poly(L-lactic acid) Foams, Polymer vol. 35, Issue 5, Mar. 1994, pp. 1068-1077.*
Kathryn, W. R.; David, J. M., Journal of Biomaterials Science, Polymer Edition 2004, 15, 1561.
Beattie, D.; Wong, K. H.; Williams, C.; Poole-Warren, L. A.; Davis, T. P.; Barner-Kowollik, C.; Stenzel, M. H., Biomacromolecules 2006, 7, 1072.
Han, C. D.; Kim, Y. W.; Malhotra, K. D., J. Appl. Polym. Sci. 1976, 20, 1583.
Lee, Y. D.; Wang, L. F., J. Appl. Polym. Sci. 1986, 32, 4639.
Klempner, D.; Sendijarevic, V.; Mikhailova Aseeva, R., Handbook of Polymeric Foams and Foam Technology, Handser-Gardner Publications Cincinatti, OH, 2004.
Klein, R. J.; Celina, M. C.; Lennart, J. L., Appl. Polym. Sci. 2010, 117, 3300.
Zalusky, A. S.; Olayo-Valles, R.; Taylor, C. J.; Hillmyer, M. A., J. Am. Chem Soc. 2001, 123, 1519.
Hou, Q.; Grijpma, D. W.; Feijen, J., Biomaterials 2003, 24, 1937.
Wei, G.; M, P. X., Biomaterials 2004, 25, 4749.
Kistler, S. S., The Journal of Physical Chemistry 1932, 36, 52.
Pekala, R. W.; Alviso, C. T.; Kong, F. M.; Hulsey, S. S., Non-Cryst. Solids 1992, 145, 90.
Pekala, R. W., Journal of Materials Science 1989, 24, 3221.
Parmenter, K. E.; Milstein, F., J. Non-Cryst. Solids 1998, 223, 179.
Katti, A.; Shimpi, N.; Roy, S.; Lu, H.; Fabrizio, E. F.; Dass, A.; Capadona, L. A.; Leventis, N., Chem. Mater. 2005, 18, 285.
Ballauff, M.; Lu, Y., Polymer 2007, 48, 1815.
Monti, F.; Fu, S.-Y.; Ilipoulos, I.; Cloitre, M., Langmuir 2008, 24, 11474.
Cammas, S.; Suzuki, K.; Sone, C.; Sakurai, Y.; Kataoka, K.; Okano, T., Journal of Controlled Release 1997, 48, 157.
Chen, Q.; Hu, Y.; Chen, Y.; Jiang, X. Q.; Yang, Y. G., Macromol. Biosci. 2005, 5, 993.
Fei, B.; Lu, H.; Xin, J. H., Polymer 2006, 47, 947.
Wang, Y.; Zhang, Y.; Wu, C.; Zhao, J., Polymer 2007, 48, 5950.
Zhang, Y.; Guan, Y.; Zhou, S., Biomacromolecules 2007, 8, 3842.
Rodriguez, B. E.; Wolfe, M. S.; Fryd, M., Macromolecules 1994, 27, 6642.
Gan, D.; Lyon, L. A., J. Am. Chem Soc. 2001, 123, 7511.
Kheirabadi, B. S.; Pusateri, A. E.; Sondeen, J. L.; Delgado, A. V.; Modrow, H. E.; Hess, J. R.; Holcomb, J. B., RTO HFM Symposium on "Combat Casualty Care in Gorund Based Tactical Siutations: Trauma Technology and Emergency Medical Procedures", St. Pete Beach, USA, 2004, p. P34 1.

(Continued)

Primary Examiner — David J Blanchard
Assistant Examiner — Sarah J Chickos
(74) Attorney, Agent, or Firm — Robert Thompson; Christos S. Kyriakou

(57) ABSTRACT

Porous polymer composites and methods of preparing porous polymer composites are provided herein. In some embodiments, a method for preparing porous polymer composites may include mixing a first polymer with a solvent and a particulate filler to form a first polymer composition, wherein the amount of particulate filler in the first polymer composition is below a mechanical percolation threshold; and removing the solvent from the first polymer composition to concentrate the first polymer and particulate filler into a second polymer composition having a porous structure, wherein the particulate filler concentration in the second polymer composition is increased above the mechanical percolation threshold during solvent removal.

21 Claims, 7 Drawing Sheets

(56) References Cited

OTHER PUBLICATIONS

Alam, H. B.; Burris, D.; DaCorta, J. A.; Rhee, P., Military Medicine 2005, 170, 63.
Albright, R. L., Reactive Polymers, Ion Exchangers, Sorbents 1986, 4, 155.
Garg, A. C.; Mai, Y.-W.; Compos. Sci, Technol. 1988, 31, 179.
Kinloch, A. J.; Shaw, S. J.; Tod, D. A.; Hunston, D. L., Polymer 1983, 24, 1341.

* cited by examiner

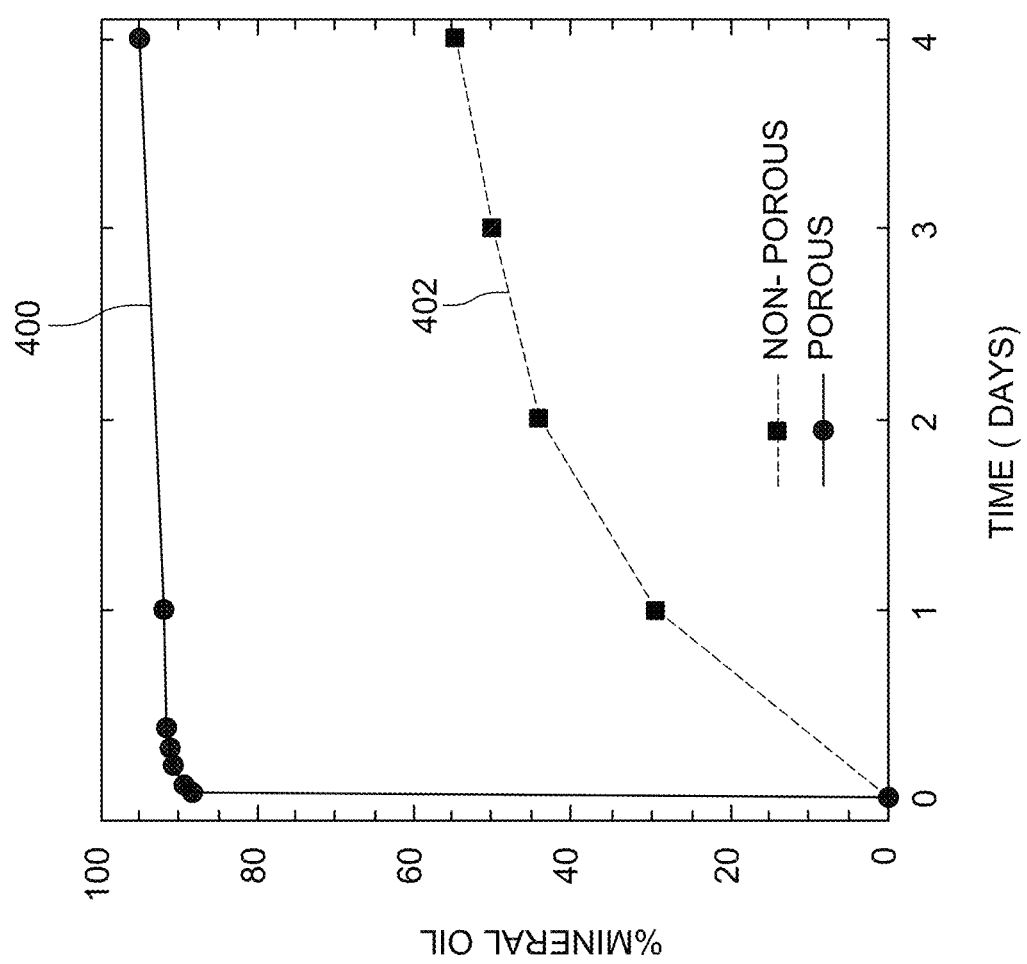

POROUS POLYMER COMPOSITES

GOVERNMENT INTEREST

The presently disclosed subject matter was made with U.S. Government support. Thus, the United States Government has certain rights in the disclosed subject matter. The embodiment described and claimed herein may be manufactured, used, sold and/or licensed by or for the United States Government without the payment royalties thereon.

CROSS REFERENCE TO RELATED APPLICATION AND PRIORITY CLAIM

This application claims priority to and the benefit of U.S. Provisional Application Ser. No. 61/883,171 filed on 26 Sep. 2013 which is incorporated herein by reference in its entirety as if fully set forth below.

TECHNICAL FIELD

Embodiments of the present invention generally relate to polymer composites and, more particularly, porous polymer composites and methods of preparing porous polymer composites.

BACKGROUND

Porous polymer composites are of significant interest due to their low density, large surface area, unique mechanical properties, tunable reactivity and mass transport properties. This combination of properties has potential utility in a variety of applications including catalyst supports, tissue surrogates, tissue scaffolding, controlled barrier/transport properties, blast mitigation materials and hybrid structural materials. For many of these applications, the performance of the porous polymer composites is directly linked with pore size and pore connectivity. For example, a decrease in the pore size at a constant pore volume will result in additional surface area, providing increased interaction with transported material. In addition, pore connectivity must be maximized to provide access to the entire pore volume.

A common way to produce porosity in a material is through the use of a foaming agent. Porosity created using a foaming agent results in a closed cell, where the air voids are completely encapsulated by a matrix. Closed cell porosity provides a decreased density but does not allow access to the air voids, thereby eliminating any mass transport through the material. To produce more open cell porosity using a foaming agent, the material must be engineered such that the pressure produced by the foaming agent is more than the cell wall can withstand. Foams have also been modified through the addition of a filler. However, the maximum filler concentration is often limited by the ability of the foaming agent to physically expand the composite matrix.

Porosity has also been incorporated into a polymer matrix through phase separation of the formulation. In these systems, the components have limited miscibility resulting in the constituents segregating into discrete regions prior to cure. After curing, one of the constituents can be preferentially etched resulting in a porous matrix of the other materials. Successful implementation of this approach requires that the constituent materials phase separate and an understanding of the phase separation kinetics. Dependent on the phase separation kinetics, an incorrect time between casting and curing can result in incomplete phase separation or macroscopic phase separation. An alternative method is to use covalently attached phase separating materials, i.e. block copolymers, where the phase separation length scale is controlled by the block length. However, block copolymers often have limited commercial availability, complex phase behavior, and slow phase separation kinetics that will limit their practical implementation.

Particulate fillers have also been incorporated into polymeric materials to produce porosity and modify material properties. One method is to use the particulate as a sacrificial poragen where the filler is incorporated into the material during cure and then etched away after cure to leave a void. To obtain interconnected pores, high poragen loadings are required to ensure direct contact between adjacent poragen prior to etching. At high loadings, the particulate will produce an exponential increase in the viscosity decreasing the ability to process the material. The limitation on particulate loading to remain processable has a large impact on the porosity, surface area, and mass transport achieved in the resulting porous polymer. In addition, the removal of the particulate eliminates the potential multi-functional benefits of incorporating the particulate into the porous backbone. Particulate has also been incorporated into phase separating systems where the particles are not involved in the development of porosity but remain in the porous structure after poragen removal. However, the particulate loading is still limited by processing difficulties and the particulate can alter the phase separation kinetics. As a result, it can be difficult to rapidly transition between different matrix materials. In addition, the particles are often embedded in the polymer to limit any multi-functionality through interaction with the transported material.

Porosity has also been obtained through hydrolysis and condensation of metal alkoxides to form aerogels consisting of alumina, silica, titanium dioxide and tin oxide. This concept has also been expanded to aqueous polycondensation reactions of organic precursors followed by pyrolosis to produce carbon aerogels. These materials have significant technological potential but have achieved limited application because the unique structure that provides the properties also results in the materials being fragile and brittle. A typical method of enhancing the mechanical toughness of the aerogel is to utilize a formulation that incorporates functional groups onto the particulate after hydrolysis and condensation of the metal oxide pre-cursor. The functional groups are then used to incorporate a conformal polymer coating on the structure to enhance the mechanical toughness of the aerogel. While the material does become more mechanically robust the process eliminates access to the particulate surface. In addition, adapting this approach to other particulates or chemistries can be challenging and may reduce the functionality of the particulate.

Porous polymer composites also have utility in hemorrhage control related products. Specific to hemorrhage control, treatment delays in combat environments can lead to infection and massive blood loss, resulting in severe consequences including death or limb amputation. In fact, hemorrhage from wounds is the leading cause of death on the battlefield. A major challenge for treatment procedures is to develop materials and delivery mechanisms that can address the various types of wounds encountered during deployment. Examples include punctures from sharp devices, bullets, or shrapnel; multiple punctures from secondary shrapnel associated with an indirect impact; massive body and limb trauma from Improvised Explosive Devices (IEDs); severe cuts and lacerations; or even large scale skin and muscle damage. In addition, wounds that are not treatable with tourniquets or compressive wound dressings such as complex groin or torso injuries are of increased concern. Due to these complications with combat casualty care, a critical need exists for therapeutic materials that are delivered locally and immediately to treat different types of battlefield wounds, until more comprehensive medical treatment is available.

Current products related to hemorrhage control fall into three general categories including: Poly-N-acetyl glucosamine (PNAG, chitin or chitosan) based dressings; zeolite or starch based powders; and fibrin based dressings. These materials generally work by absorbing water from the blood and allowing blood clotting factors to concentrate in the wound. However, additional factors such as adhesion to the wound, attraction of blood platelets, and delivery of blood clotting factors can also contribute. While each product has demonstrated effectiveness with specific types of injuries, numerous limitations hinder broad utility in combat environments including: lack of wound conformity, inability to penetrate deep wounds with complex geometry, difficulty treating large or multiple wounds, post-treatment removal of particulates, uptake of particles in arteries, cost-effectiveness, and delayed deployment. A clear need still exists for materials and treatment methods for hemorrhage control that are effective in deep wounds, stop arterial bleeding, can conform to complex wound geometry, are easily applied, and cost-effective.

Therefore, the inventors have provided improved porous particulate-loaded polymer composites and methods of preparing such porous particulate-loaded polymer composites.

SUMMARY

Embodiments of the present invention relate to methods of preparing a porous particulate-loaded polymer composite. In some embodiments, a method of forming an porous particulate-loaded polymer composite may include mixing a first polymer with a solvent and a particulate filler to form a first polymer composition, wherein the amount of particulate filler in the first polymer composition is below a mechanical percolation threshold; and removing the solvent from the first polymer composition to concentrate the first polymer and particulate filler into a second polymer composition having a porous structure, wherein the particulate filler concentration in the second polymer composition is increased above the mechanical percolation threshold during solvent removal.

In some embodiments, a method of forming a hemorrhage control product may include mixing a first polymer with a solvent and a particulate filler to form a first polymer composition, wherein the amount of particulate filler is below a mechanical percolation threshold; forming the first composition into a first geometry having a particle filler-loaded outer shell circumscribing a particle filler-loaded inner core; removing the solvent from the first polymer composition to concentrate the first polymer and particulate filler into a second polymer composition having a porous structure, wherein the particulate filler concentration in the second polymer composition is increased above the mechanical percolation threshold during solvent removal; and preferentially removing at least some of the particulate filler from the outer shell while maintaining a particulate filler-loaded inner core.

In some embodiments, a hemorrhage control product may include a porous polymer inner core comprising a particulate filler and a porous polymer outer shell circumscribing the inner core, wherein the porous outer shell is free of particulate filler.

Other and further embodiments of the invention are described in more detail, below.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 4 depicts swelling data of porous and non-porous samples in mineral oil in accordance with some embodiments of the present invention.

DETAILED DESCRIPTION

Embodiments of the present invention include porous polymer composites and methods of preparing porous polymer composites. Porous polymer composites and methods of preparing porous polymer composites, in accordance with embodiments of the present invention, advantageously allow porosity in a particle loaded polymer composite to be incorporated without the use of phase separation, poragen, or a blowing agent, advantageously allow for the incorporation of porosity to multiple particulate or polymer systems, advantageously obtain and maintain high particle loadings in a porous structure to reinforce the structure or provide additional functionality, and advantageously produce interconnected pore structure to provide mass transport through the polymer composite.

Figure 1:
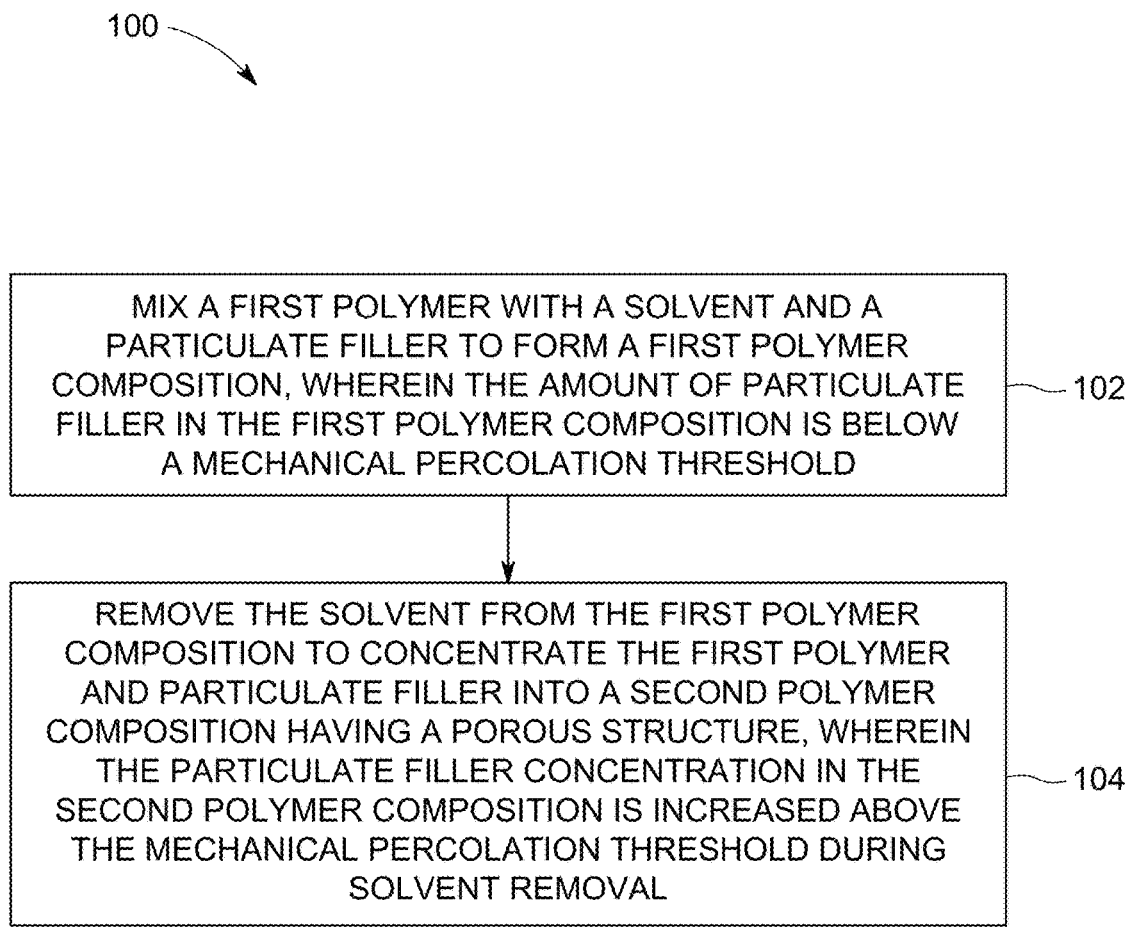
FIG. 1 depicts a flow diagram of a method of preparing a porous particulate-loaded polymer composite in accordance with some embodiments of the present invention.
Figure 2A:
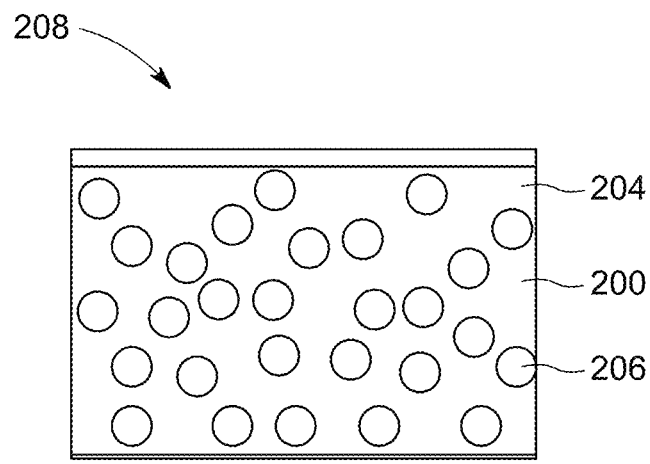
FIGS. 2A-2C depicts a schematic of a method of preparing a porous particulate-loaded polymer composite in accordance with some embodiments of the present invention.
Figure 2B:
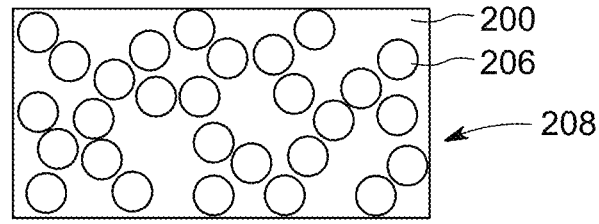
Figure 2C:
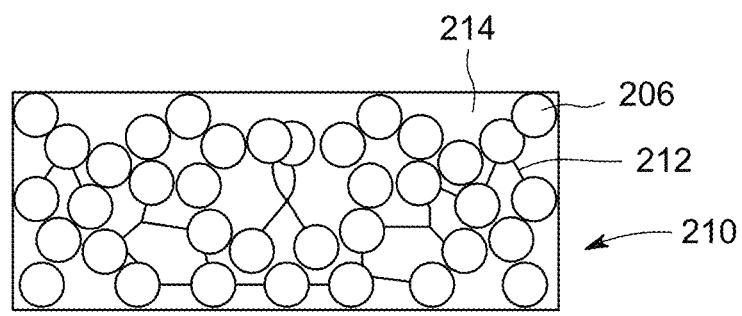

FIG. 1 depicts a flow diagram of a method 100 of forming a porous polymer composite in accordance with some embodiments of the present invention. The method 100 is schematically depicted in FIGS. 2A-2C. The method 100 starts at 102 by mixing a first polymer 200 with a solvent 204 and a particulate filler 206 to form a first polymer composition 208. The amount of particulate filler 206 in the first polymer composition 208 is below a mechanical percolation threshold. The mechanical percolation threshold is the particle concentration above which the particles in the polymer composition begin to affect each other, and thereby affect the mechanical properties of the polymer composition, such as viscosity and elasticity.

In some embodiments, the polymer 200 is either a thermoplastic or a cross-linked polymer network. Examples of thermoplastic polymers include polystyrene, polycarbonate, poly(methyl methacrylate), polyethylene, polypropylene, poly (tetrafluoro ethylene), poly (ethylene terepthalate), poly (butylene terepthalate), acrylonitrile butadiene styrene, poly (ethylene vinyl acetate), poly (vinyl alcohol, fluoro(ethylene propylene), poly(acrylates), poly(acrylonitrile), polyamide, polyaryletherketone, polybutadiene, polybutylene, polycaprolactone, poly(ether ether ketone), poly (ether ketone ketone), poly(ether imide), poly (ether sulfone), polyimide, poly(pthalamide), poly (trimethylene terepthalate), polyurethane, poly(vinyl acetate), poly (vinyl chloride), and poly (vinylidene fluoride).

The polymer network cross-linking can be physical or chemical in nature. Examples of physically cross-linked polymer networks include hydrogen bonded networks, block-copolymers, metal co-ordination cross-linking, and thermoplastic elastomers or other networks that form by phase separation or non-covalent i.e. reversible cross-linking. Chemically cross-linked polymer networks form covalent bonds between precursors. Examples of the chemical reaction used to cross-link polymer networks include epoxy, click, thiol-ene, and vinyl-silane, urethane (carbamate), diol/anhydride-vinyl (e.g. cross-linked polyesters), vulcanization/sulfur curing, and oxidative chemistries. The polymer network can also be cross-linked through a radiation source. Examples of radiation sources include gamma-radiation, electron beam, and UV light.

The particulate filler 206 can be organic or inorganic in nature. Examples of the particulate filler 206 include carbon nanotubes, silica, glass microballoons, nickel spheres, nickel nanostrands, glass beads, glass fiber, carbon black, nickel-coated carbon fiber, gold spheres, gold nanorods, calcium carbonate, titanium dioxide, carbon black, barium carbonate, magnesium carbonate, calcium hydroxide, magnesion hydroxide, aluminum oxide, zinc oxide, magnesium oxide, quartz, diatomaceous earth, calcium silicate, magnesium silicate, clay, talc, mica, asbestos, feldspar, calcium sulfate, barium sulfate, graphite, magnetite, barium ferrite, quantum dots, gallium nitride, gallium arsenic, silver, copper, and zinc. The particulate filler 206 concentration in the first polymer composition 208 is dependent on the solvent loading in the first polymer composition 208, the solvent loading after extraction in the second polymer composition 210, and the specific characteristics of the particulate including size, shape, aspect ratio, surface roughness, and surface chemistry, that have an impact on the polymer viscosity and mechanical percolation threshold. In some embodiments, the particulate filler 206 concentration in the first polymer composition 208 is about 2 volume percent to about 55 volume percent.

The solvent 204 selected is dependent on the specific chemistry of the polymer network. The selected solvent 204 must be miscible with the polymer 208. For example, in some embodiments, where the polymer is poly(styrene-b-ethylene-co-butylene-b-styrene), the solvent can be mineral oil. In some embodiments, where the polymer is a silicone elastomer, the solvent can be a silicone oil or toluene. In some embodiments, where the polymer is an epoxy elastomer or polybutadiene, the solvent can be dibutyl-phthalate. In some embodiments, where the polymer is polybutadiene, the solvent can be dibutyl-phthalate. In some embodiments, the solvent 204 concentration in the first polymer composition 208 is about 10 volume % to about 95 volume %.

Next at 104, the solvent 204 is removed from the first polymer composition 208 to concentrate the polymer 200 and particulate filler 206 into a second polymer composition 210 having a porous structure 214. As depicted in FIG. 2B, solvent removal initially causes the particulate filler 206 and first polymer 200 to concentrate until the particulate filler 206 concentration is above the mechanical percolation threshold. Further concentration of the first polymer composition 208 is frustrated by the concentrated particulate filler. As a result, the continuing removal of solvent 204 from the first polymer composition 208, as depicted in FIG. 2C, forces polymer fibrils 212 to form between the particulate filler 206, thereby generating a second polymer composition 210 having a porous structure 214. In some embodiments, the particulate filler 206 concentration in the porous second polymer composition 210 is about 3 volume percent to about 95 volume percent relative to the total volume of solids, comprised of the particulate filler and polymer, in the porous second polymer composition 210.

In some embodiments, the solvent 204 is removed from the first polymer composition 208 by evaporation in ambient conditions or through heating. In some embodiments, the solvent 204 is removed from the first polymer composition 208 by extraction using a secondary, more volatile solvent. Examples of extraction include submersion into a secondary solvent bath, soxhlet extraction, or supercritical carbon dioxide extraction. In some embodiments, the secondary solvent has a high solubility with the solvent 204 in order to extract the solvent 204 from the first polymer composition 208 but not with the first polymer 200. A secondary solvent having a high solubility with the first polymer 200 will result in a swelling of the first polymer composition 208 and a resulting loss of porosity in the polymer structure. For example, in some embodiments, where the first solvent 204 is mineral oil and the first polymer 200 is poly(styrene-b-ethylene-co-butylene-b-styrene), 1-butanol may be an effective secondary solvent having high solubility with the first solvent 204 without swelling the first polymer composition 208. Alternatively, in some embodiments, where the first solvent 204 is dibutyl pthalate and the first polymer 200 is poly(propylene glycol), water may be an effective secondary solvent having high solubility with the first solvent 204 without swelling the first polymer composition 208.

In some embodiments, about 10% to about 100% of the solvent is removed from the first polymer composition 208. In some embodiments, at least about 95% of the solvent is removed from the first polymer composition 208. In some embodiments, about 95% to about 99% of the solvent is removed from the first polymer composition 208.

In one embodiment, the polymer 200 is poly(styrene-b-ethylene-co-butylene-b-styrene), referred to as SEBS, the solvent 206 is mineral oil, and the particulate filler 208 is conductive nickel spheres and calcium carbonate. About 20 volume % of the SEBS and 80 volume percent of the mineral oil is mixed and heated to 150° C. for approximately 3 hours. Conductive nickel spheres and calcium carbonate are added at 10, 20, 30, 40, and 50 volume % of the mineral oil/SEBS mixture. The nickel nanostrands are added at 6 volume % relative to the mineral oil/SEBS mixture. The 6 volume % loading represents the maximum processsable loading of the nickel nanostrands, attributed to the significant viscosity increase due to the increased aspect ratio and surface area to volume ratio as a result of the small particle size of the nickel nanostrands. The particle loaded mixture is mixed for 15 minutes at 150° C. The mixture is cast in a rectangular mold at 135° C. and placed under vacuum to remove the air bubbles incorporated during mixing. The mixture is cooled to room temperature to form samples comprising a network of physically cross-linked polystyrene domains connected by elastic ethylene-co-butylene chains swollen with mineral oil. The mineral oil is extracted by submersing the sample in 1-butanol, which is replaced every 48 hours. The more volatile 1-butanol is removed by vacuum evaporation and the extraction progress is monitored through the sample mass loss. The extraction process is considered complete when about 95% of the mineral oil is removed.

To quantify the impact of a porous structure within a polymer composition, dried samples were placed into mineral oil to re-swell. The swelling was monitored by periodically removing the sample from the mineral oil, wiping away the excess mineral oil on the surface, and weighing the sample to determine the mass increase. To compare porous samples and non-porous samples, the mineral oil uptake was normalized to the polymer mass contained in the sample. The samples were monitored periodically over 4 days. As depicted in FIG. 4, the porous sample 400 absorbed 90% mineral oil within a few hours while the non-porous sample 402 took 4 days to reach about 50% mineral oil. This demonstrates the significant impact of porosity on the solvent absorption kinetics.

In some embodiments, the porous structure 214 of the second polymer composition 210 can be increased by removing at least some of the particulate filler 206 from the second polymer composition 210. In some embodiments, the porous structure 214 of the second polymer composition 210 can be increased by removing all of the particulate filler 206 from the porous second polymer composition 210 to produce an unfilled porous polymer. Particulate removal methods are dependent upon the specific particulate. Examples of particulate extraction methods include particulate dissolution in a solvent that will not dissolve the polymer matrix or degradation of the particulate through an external stimulus including heat, UV light, and a change in pH.

Figure 3:
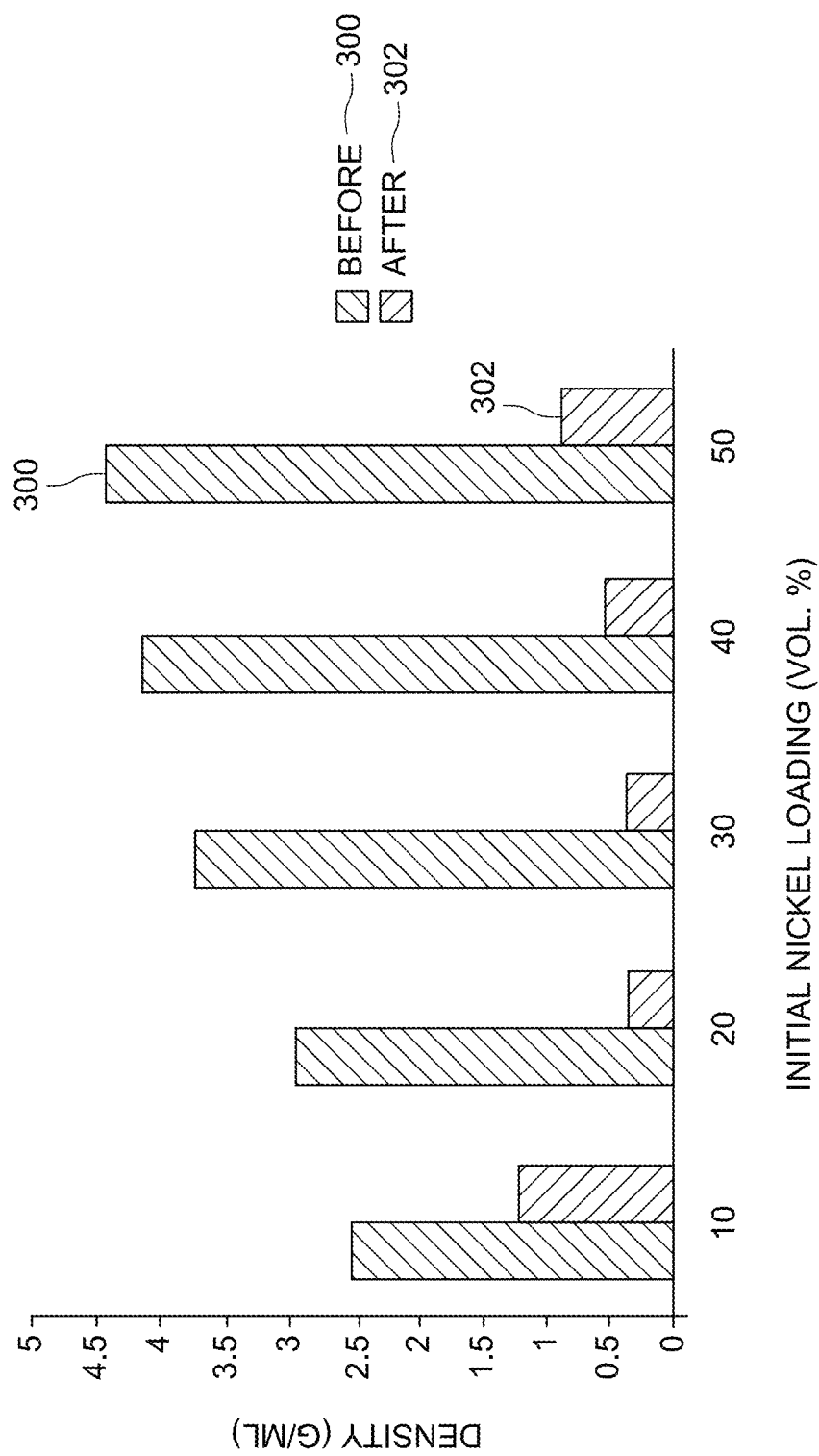
FIG. 3 depicts a graph of the reduction in density of a porous polymer composite following removal of particulate filler in accordance with some embodiments of the present invention

In the above example, after removal of the mineral oil from the polymer composition, the calcium carbonate and nickel conductive spheres are dissolved using acetic acid and hydrochloric acid, respectively. The polymer composition is submersed into the acid while monitoring the pH of the solution and the evolution of gas created from either reaction. The acid solution is replaced when the pH increases over 4 or the evolution of gas ceases. The extent of particulate removal is monitored by the change in the composite density of the polymer composition. The density is calculated by measuring the mass and dimensions of the dry polymer composite during the particulate extraction. FIG. 3 shows the change in density of a porous composite as a function of initial nickel loading in the solvent-swollen elastomer before etching 300 out the nickel with hydrochloric acid and after etching 302 out the nickel with hydrochloric acid.

In some embodiments, the properties of the porous polymer composites described above can further be modified by backfilling the porous structure with a secondary polymer to enhance the toughness of the composite, control strain rate dependent mechanical properties, and tailor the mechanical response for a specific application.

One specific application where a porous polymer composition can be backfilled with a second polymer is in the production of pre-impregnated film adhesives with high filler loadings. In the production of such film adhesives, the porous polymer composition can be backfilled with a thermoplastic or thermosetting adhesive to impart adhesive bonding capability, such as epoxies, vinyl esters, acrylates, methacrylates, polyurethanes, silicones, cyanate esters, natural rubber, polychloroprene, poly(vinyl acetate), ethylene-vinyl-acetate, or the like. In some embodiments, functional groups may be covalently bonded to the porous structure of the polymer composition. The functional groups advantageously improve the interaction between the backfilled second polymer and the porous polymer composition. In some embodiments, the functional group is at least one of maleic anhydride, hydroxyl, amine, epoxy, carboxylic acid, thiol, metal ligand, silane, azide, alkene, alkyne, or diels alder adduct.

In one example, 20 volume % SEBS and 80 volume % mineral oil are mixed and heated to 150° C. for 3 hours. Alumina is added to the mineral oil/SEBS mixture incrementally until reaching a final concentration of 75 volume %. The mixture is cast into discs approximately 7.5 cm in diameter and 1 cm thick and cooled to room temperature. The 1 cm thick discs are placed in a hot press between two smooth aluminum plates treated with a release agent. Steel spacers of 0.85 mm thickness are put in between the plates to set the thickness of the film. A pressure of approximately 150 kPA is applied to the aluminum plates while incrementally increasing the temperature to 100° C. As the discs began to flow in the plates, the pressure is adjusted until the aluminum plates contact the steel spacers to ensure a uniformly thick film.

The mineral oil is extracted from the film by submersing the sample in 2-propanol, which is replaced every 24 hours. The extraction progress is monitored through the sample mass loss. The extraction process is considered complete when about 95% of the mineral oil is removed.

To backfill the network of pores in the film, a low viscosity epoxy (about 15 cP at 80° C.) is chosen, comprising a diglycidyl ether of bisphenol-A (Epon 815c) and polyoxypropylene-diamine (Epikure 3230). To begin backfilling, the film is placed in an epoxy resin bath at 80° C. The resin bath, which contains a significant amount of excess epoxy, is then placed in a pressurized vessel at 375 kPa for 45 minutes. The samples are then cured at 80° C. for at least 12 hours and post-cured at 120° C. for 2 hours.

The adhesive properties of film are measured using lap shear joints. The epoxy adhesive yields a lap shear strength of 25.1±0.4 MPa, while the backfilled alumina adhesive produces an expected decrease to 10.6±0.6 MPa, corresponding to 42% of the neat epoxy adhesive strength. The backfilled adhesive system contains 32.5 volume % epoxy, 20 volume % SEBS, and 47.5 volume % alumina. Since the alumina and SEBS contribute minimally to the bond strength, the bond strength in the adhesive film is solely dependent on the bond strength and concentration of the backfilled adhesive.

Since adhesive processing at high filler loadings becomes difficult due to increased viscosity and large aggregates, and results in overly brittle adhesives; the process described above advantageously solves the issues of adhesive processing and poor mechanical properties for highly loaded systems. In the example above, the alumina filler is processed into a co-continuous morphology with a porous network and is connected by a thermoplastic polymer which helps maintain the toughness of the adhesive system and the porous network is backfilled with a thermoplastic or thermosetting adhesive to impart adhesive bonding capability.

In some embodiments, the first polymer composition is formed into a first geometry having a particulate filler-loaded outer shell circumscribing a particulate filler-loaded inner core. In some embodiments, the first geometry is one of an elongated strand, a sheet, a particle, a film, or a bead. In some embodiments, the first composition can be applied to fabrics, adhesive strips, or gauze. In some embodiments, at least some of the particulate filler from the outer shell is preferentially removed while maintaining a particulate filler-loaded inner core.

Figure 5C:
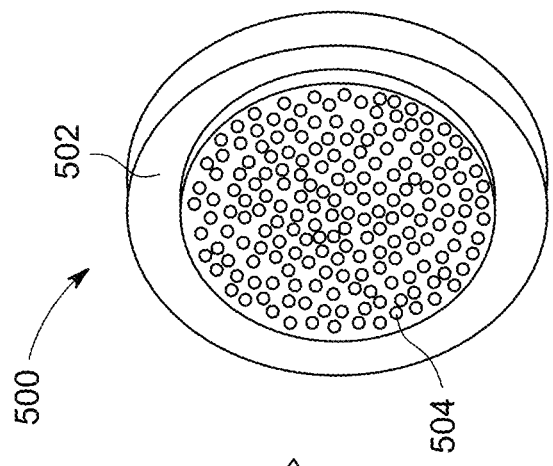
FIGS. 5A-5C depicts a hemorrhage control product in accordance with some embodiments of the present invention.
Figure 5B:
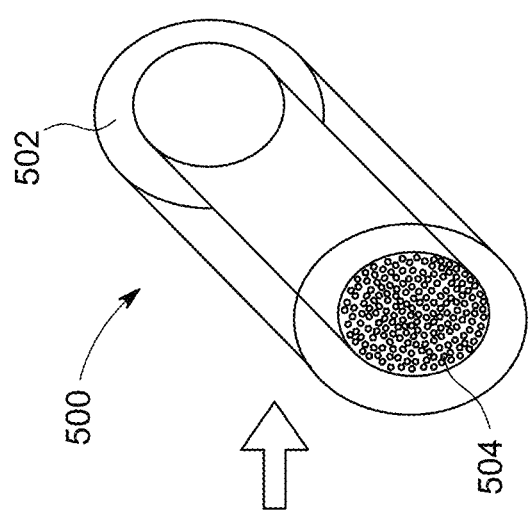
Figure 5A:
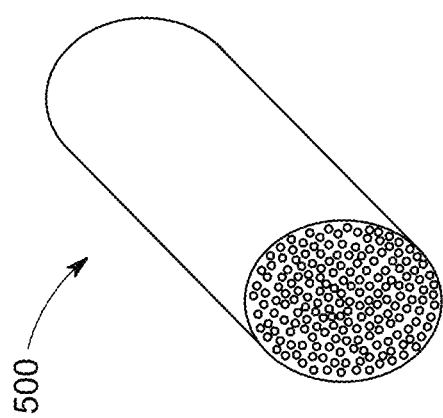

In some embodiments, as depicted in FIG. 5A, the first polymer composition is extruded into an elongated strand 500 having a particulate filler-loaded outer shell 502 circumscribing a particulate filler-loaded inner core 504 is in the formation of hemorrhage control related products. Following the removal of solvent from the elongated strand 500 in the manner described above, at least some of the particulate filler from the outer shell 502 is preferentially removed while maintaining a particulate filler-loaded inner core 504.

The hemorrhage control products formed by the method described above advantageously maintains water-swelling under pressures relevant to physiological conditions while remaining conformable to the wound cavity. Furthermore, the ability to incorporate porosity using any network chemistry, cross-link density, and particulate advantageously enables the hemorrhage control product the ability to balance the mechanical properties of the scaffold with the degree of water swelling. In addition, the incorporation of porosity into a hemorrhage control product enhances the swelling kinetics allowing the product to be effective on a shorter timescale. This concept can be further enhanced through the development of a core-shell scaffold where the inner core will remain mechanically robust to maintain swelling under pressure while the outer core will be soft and conformable to enable complete packing of a complex wound tract. This can be accomplished through time-resolved particulate extraction from the porous scaffold where the particulate near the edges are preferentially extracted leaving an unfilled porous shell and a highly particle loaded porous core.

Figure 6:
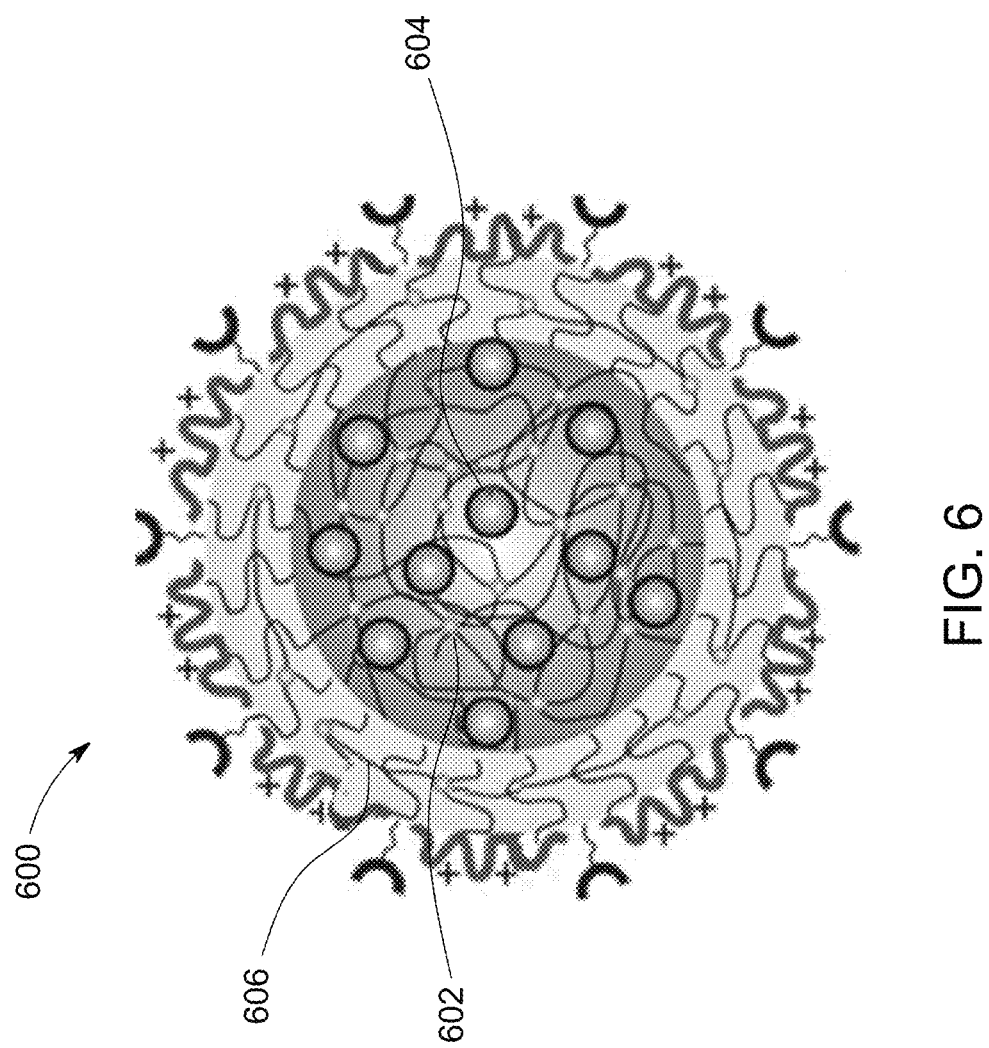
FIG. 6 depicts a core-shell structure of a hemorrhage control product in accordance with some embodiments of the present invention.

FIG. 6 depicts a schematic of core-shell structure 600 of a hemorrhage control product comprising a porous polymer inner core 602 loaded with a particulate filler 604 and a porous polymer outer shell 606 circumscribing the inner core 602, wherein the porous polymer outer shell 606 is free of particulate filler 604.

Modifications to the core-shell structure 600 may improve its hemorrhage control effectiveness. For example, the core-shell structure may be modified to provide the hemorrhage control product the ability to adhere to the wound cavity, thereby enabling the product to seal the wound cavity to decrease bleeding. This can be accomplished through the incorporation of explicit chemical functionality, such as relevant proteins, dopamine, catechol, glutaraldehyde and other relevant biological adhesives, or as the result of enhanced tack adhesion as the result of water swelling. In some embodiments, the core-shell structure 600 may be modified to include biocompatible foaming agents to produce rapid expansion and application of pressure. Examples of biocompatible foaming agents include peroxide and lyseine derived isocyanates that will produce $CO_2$ in the presence of water. In some embodiments, the core-shell structure 600 may be modified to incorporate controlled release capsules to deliver clotting factors and therapeutic agents. In some embodiments, the surface of the core-shell structure 600 may be modified with chitosan, a bio-derived polycationic material that has shown efficacy for use in hemorrhage control. In some embodiments, the polymer chemistry, cross-link density, and the chemistry of the pore surface may be modified to enhance the equilibrium swelling.

In one example, a hemorrhage control product is formed by mixing 20 volume % SEBS and 80 volume % mineral oil and heated the mixture to 150° C. for 3 hours. Calcium carbonate is added at 34 volume % of the mineral oil/SEBS mixture and mixed until cooled. The material is subsequently mixed using a twin screw extruder at 110° C. for 15 minutes at 50 rpm prior to extrusion. The extruded strand is then processed as is or cast into a rectangular mold at 135° C. and placed under vacuum to remove the air bubbles incorporated during mixing. The samples are cooled to room temperature to form a network of physically cross-linked polystyrene domains connected by elastic ethylene-co-butylene chains swollen with mineral oil. The mineral oil is extracted from the samples by submersing the sample in 1-butanol. The 1-butanol is replaced every 48 hours. The more volatile 1-butanol is removed by vacuum evaporation and the extraction progress was monitored through the sample mass loss. The extraction process is considered complete when about 95% of the mineral oil is removed.

To remove the calcium carbonate, resulting in an unfilled porous elastomer scaffold, the material is submersed in acetic acid while monitoring the pH of the solution and the evolution of gas. The acid solution is replaced when the pH increases over 4 or the evolution of gas ceases. To obtain an unfilled shell while retaining a filled core, the sample is extracted for a set period of time and then rinsed in pure water to eliminate further dissolution. The extent of particulate removal is quantified through mass loss of the sample.

To determine the impact of acid extraction time, discs 8 mm in diameter and about 3 mm thick are cut out of the mineral oil extracted sheet. The discs are then cut in half, with one half placed in 1 M acetic acid for 2, 5, 24, or 48 hours, and the other half retained for comparison. After acid exposure, the samples are removed from the acetic acid, washed with water, and dried. To visualize the impact of the acetic acid on the microstructure, the samples are swollen in mineral oil. The shell thickness can be controlled through acid exposure time and the high degree of mineral oil swelling. The required exposure time can be reduced by increasing the acid concentration.

Figure 7:
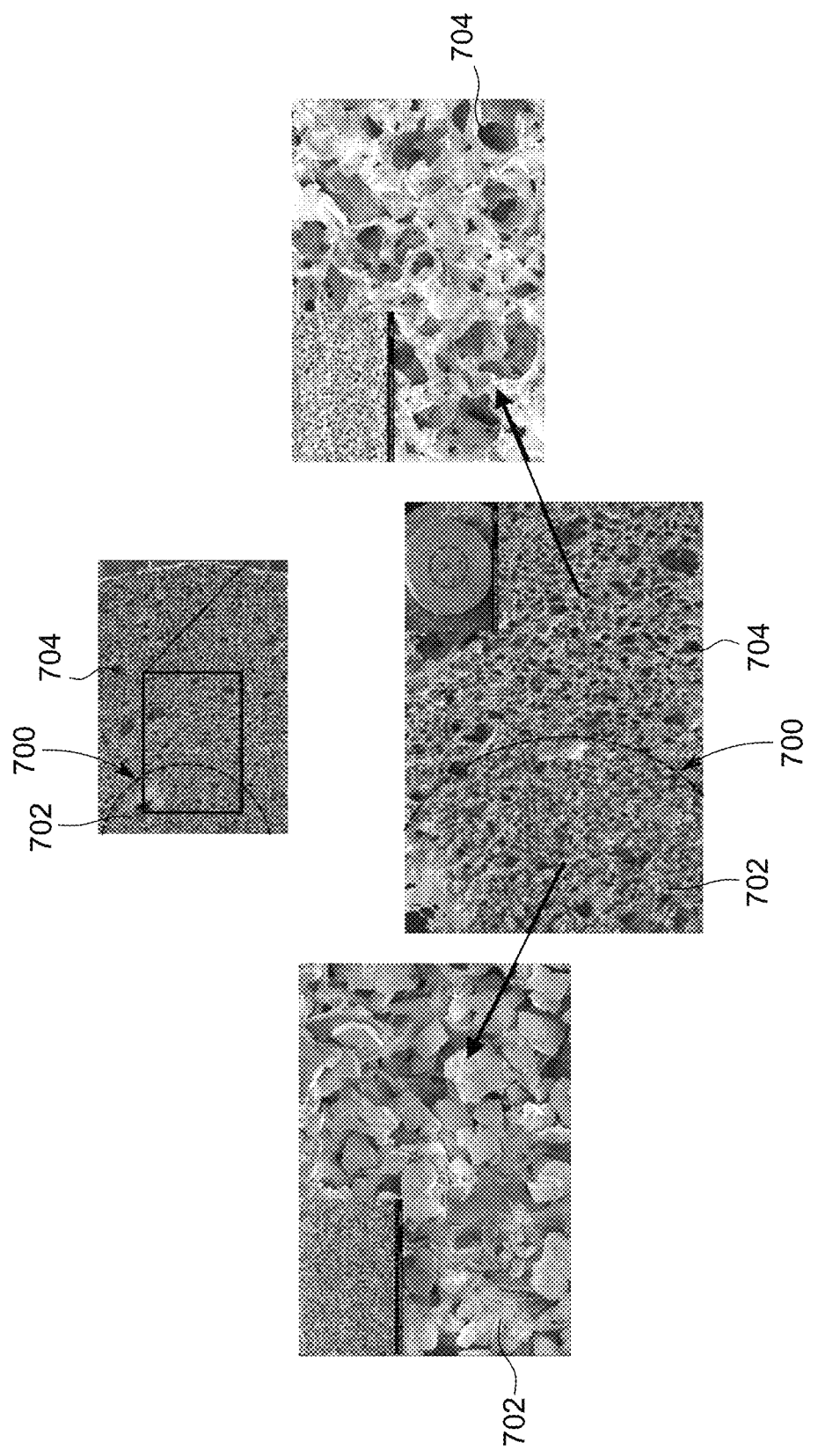
FIG. 7 depicts a hemorrhage control product in accordance with some embodiments of the present invention.

To demonstrate the ability to continuously process the scaffold material, the extruded polymer composite strands undergo mineral oil extraction followed by acid extraction of 24 and 48 hours, respectively. The strand is then cut into discs about 4 mm in diameter. The complete extraction of calcium carbonate from the outer core is readily apparent in the SEM images of the core-shell discs depicted in FIG. 7. FIG. 7 depicts SEM images of a disc with a inner core highly loaded with calcium carbonate and an outer shell of porous elastomer that does not contain calcium carbonate. The dashed line 700 denotes the boundary between the filled core 702 and extracted shell 704.

In a second example, SBS (6 g) is mixed with acrylic acid and t-butyl acrylate (10.11 g), respectively, at monomer to butadiene molar ratios of 1:1, 2:1, and 4:1 along with 7 mol % of a photoinitator, 2,2 diethoxyacetophenone (0.6 g), relative to the butadiene mol % in 500 mL of toluene. The samples are irradiated with a 75 mW/cm2 W UV lamp for 60 minutes. SBS polymers, modified with tert-butyl acrylate (SBS-tBA) and acrylic acid (SBS-AA), are washed in isopropanol and water, respectively, to remove unreacted monomer.

To enhance water swelling, the inherently hydrophobic polymer can be modified with hydrophilic polymer chains or chemical functionality. This can be accomplished by modifying the polymer prior to processing or after the production of the porous structure. The advantage of modification after the porous structure formation is that the established processing conditions can still be utilized. However, the modification conditions have to be carefully selected to produce uniform modification of the entire internal surface and avoid pore collapse. Alternatively, modification prior to processing provides better control of the modification but may impact the ability to process the material.

Initial modifications have focused on modifications prior to processing due to the greater flexibility with reaction conditions. Specifically, modification of the SBS with poly (acrylic acid), commonly used as a biocompatible and superabsorbent polymer. The modification is being explored by two synthetic routes: 1) grafting of poly(acrylic acid) SBS and 2) grafting of poly (tert-butyl acrylate) that can be acid cleaved to produce poly(acrylic acid), respectively, to the butadiene block of the SBS. Upon grafting poly(acrylic acid) to SBS (SBS-AA) the material exhibited a 100 wt % increase in water swelling however, the material no longer swells in mineral oil, the solvent that has been used for processing. Due to the high processing temperature, water cannot be utilized for processing and another low volatility solvent must be identified for processing. Examples of low volatility hydrophilic solvents include ethylhexanol and dodecanol. Alternatively, SBS functionalized with tert-butyl acrylate (SBS-tBA) exhibited very little water swelling and maintained a high degree of water swelling. Upon exposure to acetic acid, the SBS-tBA exhibited a 120 wt % increase in water swelling attributed to the cleavage of the t-butyl groups to produce poly(acrylic acid). This allows for the use of the same processing conditions as the unmodified polymer and, after pore formation, the tert-butyl groups can be cleaved to produce acrylic acid.

While the foregoing is directed to embodiments of the present invention, other and further embodiments of the invention may be devised without departing from the basic scope thereof.

The invention claimed is:

1. A method of forming a porous polymer composition without the use of phase separation, a poragen or a blowing agent, comprising:
    mixing a first polymer with a first solvent that is miscible with said first polymer and a particulate filler at a first concentration to form a first polymer composition, wherein the first concentration of particulate filler in the first polymer composition is below a mechanical percolation threshold;
    removing the first solvent from the first polymer composition to concentrate the first polymer and the particulate filler into a second polymer composition having a porous structure, wherein the particulate filler concentration in the second polymer composition is increased above the first concentration and the mechanical percolation threshold during first solvent removal;
    wherein the first polymer is poly(styrene-b-ethylene-co-butylene-b-styrene); and
    further wherein removing the first solvent from the polymer composition concentrates that filler in the first polymer above the mechanical percolation threshold of the filler in the first polymer forcing fibrils to form between filler particles and the produces a porous polymer composition with an interconnected pore structure that provides mass transport through the polymer composition without the use of phase separation, a poragen or a blowing agent.

2. The method of claim 1, wherein the particulate filler concentration in the first polymer composition is about 2 volume % to about 55 volume %.

3. The method of claim 1, wherein the particulate filler concentration in the second polymer composition is about 3 volume % to about 95 volume % relative to a total volume of solids in the second polymer composition.

4. The method of claim 1, wherein the first solvent is removed by at least one of evaporation or extraction with a secondary solvent.

5. The method of claim 1, further comprising backfilling the second polymer composition with a second polymer.

6. The method of claim 1, further comprising removing at least some of the particulate filler from the second polymer composition.

7. The method of claim 6, further comprising removing the particulate filler from the second polymer composition by at least one of degrading the particulate filler through the application of an external stimulus to the second polymer composition or dissolving the particulate filler for in a first solvent which will not dissolve the first polymer.

8. The method of claim 1, further comprising extruding the first polymer composition into an elongated strand having a particulate filler-loaded outer shell circumscribing a particulate filler-loaded inner core.

9. The method of claim 8, further comprising preferentially removing at least some of the particulate filler from the outer shell while maintaining a particulate filler-loaded inner core.

10. The method of claim 1, further comprising mixing chemical additives into the first polymer composition.

11. The method of claim 10, wherein the chemical additives further comprise at least one of proteins, dopamine, catechol, glutaraldehyde, peroxide, clotting agents, therapeutic agents, or chitosan.

12. A method of forming a hemorrhage control product without the use of phase separation, a poragen or a blowing agent, comprising:
    mixing a first polymer with a first solvent that is miscible with said first polymer and a particulate filler at a first concentration to form a first polymer composition, wherein the first concentration of particulate filler is below a mechanical percolation threshold;
    forming the first polymer composition into a first geometry having a particle filler-loaded outer shell circumscribing a particle filler-loaded inner core; and
    removing the first solvent from the first polymer composition to concentrate the particulate filler into a second polymer composition having a porous structure, wherein the particulate filler concentration in the second polymer composition is increased above the first concentration and the mechanical percolation threshold during first solvent removal
    wherein the first polymer is poly(styrene-b-ethylene-co-butylene-b-styrene).

13. The method of claim 12, further comprising preferentially removing the particulate filler by degrading the particulate filler through the application of an external stimulus to the porous second polymer composition.

14. The method of claim 13, further comprising preferentially removing the particulate filler from the outer shell by dissolving the particulate filler for a first period of time in a second solvent which will not dissolve the first polymer.

15. The method of claim 12, further comprising mixing at least two of proteins, catechol, glutaraldehyde, peroxide, clotting agents, therapeutic agents, or chitosan into the first polymer composition.

16. An article, made by the method of claim 1.

17. The article of claim 16, further comprising at least two of proteins, dopamine, catechol, glutaraldehyde, peroxide, clotting agents, therapeutic agents, biocompatible foaming agents, or chitosan bonded to an outer surface of the porous polymer outer shell to promote wound healing.

18. The article of claim 16, further comprising a thermosetting adhesive bonded to the porous polymer outer shell to promote adhesive bonding.

19. The method of claim 1, wherein the first solvent is an oil that that is miscible with said first polymer.

20. The method of claim 1, wherein the first solvent is a mineral oil that that is miscible with said first polymer.

21. The method of claim 1, further comprising removing the first solvent with a second solvent that has high solubility with the first solvent but without swelling the first polymer composition.

* * * * *